US007022637B2

(12) United States Patent
Song et al.

(10) Patent No.: US 7,022,637 B2
(45) Date of Patent: Apr. 4, 2006

(54) SELECTIVE METHYLATION CATALYST, METHOD OF CATALYST MANUFACTURE AND METHYLATION PROCESS

(75) Inventors: Chunshan Song, State College, PA (US); Jian-Ping Shen, State College, PA (US); Lawrence D. Lillwitz, Yorkville, IL (US)

(73) Assignees: BP Corporation North America Inc., Warrenville, IL (US); The Pennsylvania State University, University Park, PA (US)

( * ) Notice: Subject to any disclaimer, the term of this patent is extended or adjusted under 35 U.S.C. 154(b) by 474 days.

(21) Appl. No.: 09/771,876

(22) Filed: Jan. 29, 2001

(65) Prior Publication Data

US 2005/0054889 A1  Mar. 10, 2005

(51) Int. Cl.
*B01J 29/06* (2006.01)
(52) U.S. Cl. .......................................... 502/64; 502/66
(58) Field of Classification Search .................. 502/64, 502/66, 71, 74, 77, 61, 78, 79; 423/713, 423/715
See application file for complete search history.

(56) References Cited

U.S. PATENT DOCUMENTS

| 4,443,552 A | * | 4/1984 | Iida et al. ...................... 502/66 |
| 4,446,008 A | * | 5/1984 | Shimakawa et al. ..... 208/111.15 |
| 4,638,105 A | * | 1/1987 | Chang et al. ................ 585/481 |
| 4,837,397 A | * | 6/1989 | Absil et al. ..................... 502/66 |
| 4,957,891 A | * | 9/1990 | Sachtler et al. ................ 502/61 |
| 4,994,254 A | * | 2/1991 | Suzuki et al. ................ 423/713 |
| 5,098,687 A | * | 3/1992 | Skeels et al. ................ 423/715 |
| 5,207,893 A | * | 5/1993 | Iwamoto et al. ........ 208/111.15 |
| 5,411,724 A | * | 5/1995 | Beyer et al. ............. 423/328.2 |
| 5,518,708 A | * | 5/1996 | Skeels et al. ................ 423/713 |
| 5,614,079 A | * | 3/1997 | Farnos et al. .................. 208/27 |
| 5,648,585 A | * | 7/1997 | Murray et al. ............... 585/671 |
| 5,925,329 A | * | 7/1999 | Williams et al. ............ 423/700 |
| 5,993,764 A | * | 11/1999 | Tabata et al. ............ 423/239.2 |

FOREIGN PATENT DOCUMENTS

JP  4-360842  * 12/1992
JP  AA 6329564  11/1994

OTHER PUBLICATIONS

Michael Sigl; Ernst Stefan; Jens Weitkamp; Helmut Knozinger. Characterization of the acid properties of [Al]-,[Ga]— and [Fe]—HZSM—5 by low-temperture FTIR spectroscopy of adsorbed dihydrogen and ethylbenzene disproportionation. Copyright 1998. (Abstract only.).

A. Chatterjee; A. K. Chandra. Fe and B substitution in ZSM-5 zeolites: A quantum-mechanical study. Copyright 1998. (Abstract only.).

Juergen, Mueller. Investigations of the thermal decomposition of PVC in the presence of metal chlorides. Copyright 1998. (Abstract only.).

S. J. Kulkarni; K. V. V. S. B. S. R. Murthy; K. Nagaiah; V. Sylesh Kumar; Y. V. Subba Rao; M. Subrahmanyam; A. V. Rama Rao. Alkylation of naphthalene with methanol over modified zeolites. Copyright 1998. (Abstact only.).

Derwent Information Ltd. 2,6- or 2,7-Di alkyl naphthalene highly selective and efficient prodn.—by reacting naphthalene cpd. and alkylating agent in presence of specific zeolite treated in soln. of organic silane, for high mol. material. Copyright 1998. (Abstract only.).

Shu-Bin Pu: Tomoyuki Inui. Synthesis of 2,6-dimethylnaphthalene by methylation of methylnaphthalene on various medium and large-pore zeolite catalysts. pp. 305-316. Mar. 12, 1996.

T. Komatsu; Y. Araki; S. Namba; T. Yashima. Selective formation of 2,6-dimethylnaphthalene from 2-methylnaphthalene on ZSM-5 and metallosilicates with MFI structure. pp. 1821-1828. 1994.

* cited by examiner

*Primary Examiner*—Jonathan Johnson
(74) *Attorney, Agent, or Firm*—Scott P. McDonald; Nirav Patel

(57) ABSTRACT

Novel catalysts and processes in accordance with the invention can accomplish high selectivity and conversion of naphthalenic compounds such as the conversion of methylnaphthalene (2-MN) or naphthalene to 2,6-dimethylnaphthalene (2,6-DMN). The catalysts are prepared by treating, for example, a ZSM-5-type material with iron in the presence of a halogen such as a fluoride. The resulting catalyst includes iron, as well as a significant portion of aluminum present in the ZSM-5-type starting material. Processes for using the catalysts also are disclosed.

2 Claims, 5 Drawing Sheets

SELECTIVE METHYLATION CATALYST, METHOD OF CATALYST MANUFACTURE AND METHYLATION PROCESS

BACKGROUND OF THE INVENTION

Dialkylnaphthalenes are useful in a wide variety of commercial applications. Certain dialkylnaphthalenes, such as 2,6-dimethylnaphthalene (2,6-DMN), are particularly useful as intermediates in the synthesis of 2,6-dimethyldicarboxylate (2,6-NDC) and 2,6-naphthalenedicarboxylic acid (2,6-NDA). Both 2,6-NDC and 2,6-NDA can be used in the manufacture of polymers such as polyethylenenaphthalate (PEN) and various copolymers of naphthalates and other materials, such as polyethyleneterephthalate (PET).

Polymers of 2,6-NDC and 2,6-NDA or copolymers incorporating these monomers ("2,6-polymers") are known to be useful in a wide variety of commercial applications.

Films and fibers made from 2,6-polymers exhibit strength and thermal properties which are superior to films and fibers made from other polymers such as PET. These enhanced properties have led to the use of 2,6-polymers in camera films and magnetic recording tapes as well as electrical and electronic components.

2,6-polymers also exhibit high resistance to the diffusion of gases such as carbon dioxide, water vapor and oxygen. This resistance to gas diffusion makes these polymers useful in films and containers for a wide variety of food and beverage packaging applications.

The superior physical strength of 2,6-polymers also renders these polymers useful in physically demanding applications such as cords for automobile and motorcycle tires.

Unfortunately, the commercial scale synthesis of monomers such as 2,6-NDC is a complex, multi-step process. This complex process can result in a relatively high price per pound for 2,6-NDC when compared to other monomers.

The synthesis of 2,6-NDC typically includes several steps. In a typical synthesis, orthoxylene and butadiene are reacted over an alkali metal or other catalyst to yield a 5-orthotolyl pentene (5-OTP) alkenylation product. The 5-OTP is then cyclized over an acid catalyst to yield 1,5 dimethyltetralin (1,5-DMT). The 1,5 DMT is dehydrogenated over a noble metal or other dehydrogenation catalyst to yield 1,5 dimethylnaphthalene (1,5-DMN), which is subsequently isomerized to produce 2,6-DMN.

Once 2,6-DMN has been produced, it can be oxidized to produce 2,6-NDA, which is subsequently esterified to produce 2,6-NDC. This 2,6-NDC can then be polymerized in the presence of, for example, ethylene glycol, to produce PEN useful as a polymer or copolymer in applications such as those discussed above.

The foregoing seven step process to produce PEN demands that every synthesis step be selective and produce high yields of the desired end product if NDC is to be manufactured in a commercially successful manner.

Alternative synthesis schemes are desired to improve yields or reduce the number of steps required to produce monomers such as 2,6-NDC and 2,6-NDA. One such synthesis scheme includes the process step of the selective methylation of 2-monomethyl naphthalene (2-MN) directly to 2,6-DMN. Efficient conversion of 2-MN to 2,6-DMN requires the use of highly selective, high yield catalysts to render synthesis routes using this step economically attractive.

For example, Japanese patent document JP 6329564 describes the use of a ZSM-5 type ferrisilicate catalyst, obtained by direct hydrothermal synthesis, which is useful for the selective methylation of 2-MN. In this catalyst, iron is contained in the framework of the silicate, instead of aluminum. In other words, iron replaces substantially all of the aluminum present in the traditional ZSM-5 aluminosilicate framework. This process results in a catalyst type commonly referred to as an "Fe-MFI"-type catalyst. As described in this reference, such catalysts can provide for improved selective methylation of 2-MN when at least 80 percent, and preferably 90 or more percent, of the metal in the zeolitic lattice structure is iron.

The methylation performance of such an Fe-MFI catalyst obtained by direct hydrothermal synthesis is described below by Komatsu, et al., in an article titled "Selective Formation of 2,6-Dimethylnaphthalene from 2-Methylnaphthalene on ZSM-5 and Metallosilicates with MFI Structure" published in Zeolites and Related Microporous Materials: State of the Art 1994, Studies in Surface Science and Catalysis, Vol. 84, pages 1821–1828, Elsevier Science B.V. (1994). In this article, Komatsu et al. describe the use of their Fe-MFI catalyst to obtain about a 13 percent conversion of 2-MN, a selectivity to 2,6-DMN of about 49 percent, and a ratio of 2,6-DMN to 2,7-DMN in the converted product of about 1.7 to 1. The selectivity represented by a ratio of 2,6-DMN to 2,7-DMN of about 1.7, together with the reported overall conversion of 2-MN to 2,6-DMN of just over six percent in a methylation step, reported both in the Japanese patent and the article by Komatsu et al., are believed to be too low to enable an economically viable synthesis scheme incorporating this conversion step.

A similar methylation scheme is disclosed by Shu-Bin Pu and Tomoyuki Inui in their paper titled "Synthesis of 2,6-Dimethylnaphthalene by Methylation of Methylnaphthalene On Various Medium and Large-Pore Zeolyte Catalysts," Applied Catalysis A: General 146, pages 305–316, Elsevier Science B.V. (1996).

Pu and Inui report a 2.9 percent conversion of 2-MN, with a selectivity for 2,6-DMN of about 48 percent, and a 2,6-DMN to 2,7-DMN ratio of about 1.5 using Fe-MFI catalyst obtained by direct hydrothermal synthesis. As with Komatsu's catalyst, while the use of iron in place of aluminum in the zeolitic lattice structure shows promise in terms of selectivity for 2,6-DMN, the combination of conversion and selectivity is believed to be insufficient to be economically viable.

What is needed is an improved catalyst for the selective conversion of 2-MN to 2,6-DMN that will provide a substantially higher yield of 2,6-DMN, so that a 2,6-NDC synthesis scheme incorporating this step can be commercially viable.

SUMMARY OF THE INVENTION

Surprisingly, we have found that high selectivity and conversion of 2-MN to 2,6-DMN can be accomplished by novel catalysts and processes which involve treating a zeolitic material with iron and/or other additional metals in the presence of a halogen such as a fluoride. The resulting catalysts include iron or the other additional metal, but a significant portion of aluminum present in the zeolitic starting material remains in the catalyst.

In a first embodiment of our invention, a catalyst for methylating a naphthalenic feedstock is disclosed. The catalyst is a zeolitic material incorporating Al and one or more additional metals selected from the group consisting of Fe, Ga, Ti and Co, and mixtures thereof. The molar ratio of additional metal(s) to Al is between about 1:10 and 3:1. In some preferred embodiments, the catalyst includes between 0.01 and 5 weight percent of a noble metal such as platinum or palladium. A portion of acid catalyst sites in the catalyst can be intentionally deactivated prior to use of the catalyst for improved stability over long catalyst run times.

A second embodiment of our invention is a method for preparing an isomorphically-substituted zeolitic catalyst. The catalyst is prepared an aluminosilicate zeolitic material such as ZSM-5, ZSM-11, ZSM-12, ZSM-22, MCM-22, ZSM-23, ZSM-39, ZSM-57, mordenite, Beta, FAU, and L-types. The aluminosilicate material is slurried with a soluble metal compound and refluxed under conditions effective for substituting aluminum in the aluminosilicate zeolitic material with metal from the soluble metal compound to yield a catalyst having a metal to aluminum ratio of between 1:10 and 3:1. Preferably, the process is conducted in the presence of a soluble hydrogen fluoride salt such as $NH_4HF_2$.

In other embodiments of the invention, catalysts are prepared in which iron is directly substituted in the aluminosilicate matrix of a ZSM-5 material to form a metallosilicate matrix in which the iron to metal ratio in the resulting metallosilicate matrix is from between about 1:10 to 3:1.

Catalysts in accordance with our invention can provide about twenty percent conversion of 2-MN, with approximately sixty percent selectivity for 2,6-DMN, thereby substantially improving the yield of 2,6-DMN available from a selective methylation step when compared to Fe-MFI type catalysts in which virtually all the aluminum in the lattice structure has been replaced by iron.

Preferred embodiments of the catalysts prepared by our process in which the iron to aluminum ratio ranges from about 0.25 to 1.5 can provide 2,6-DMN to 2,7-DMN ratios of between about 1.8 and 2.2, thereby further simplifying separation of the somewhat difficult to separate 2,6-DMN and 2,7-DMN isomers.

The higher 2,6-DMN to 2,7-DMN ratios enabled by our invention are important in subsequent purification steps because these two materials form a eutectic mixture of 2,7-DMN to 2,6-DMN of about 1.5:1. Therefore, to obtain appreciable yields of 2,6-DMN per pass in a crystallization purification process, the 2,6- to 2,7-ratio should be as high as possible above 1.5:1. Alternatively, in an absorption type purification process, such as a UOP SORBEX process in which 2,7-DMN would be the absorbed component, the higher 2,6-DMN to 2,7-DMN ratio requires less solvent extraction activity to reject undesired 2,7-DMN.

Thus, in yet another embodiment of the invention, we methylate a naphthalenic feedstock in the presence of a methyl group donor under methylation conditions in the presence of a catalyst of the types discussed above. Preferably, the naphthalenic feed stock will be naphthalene or 2-methyl naphthalene, and the methyl group donor will be methanol or dimethyl ether.

DESCRIPTION OF THE PREFERRED EMBODIMENTS

Figure 1A:
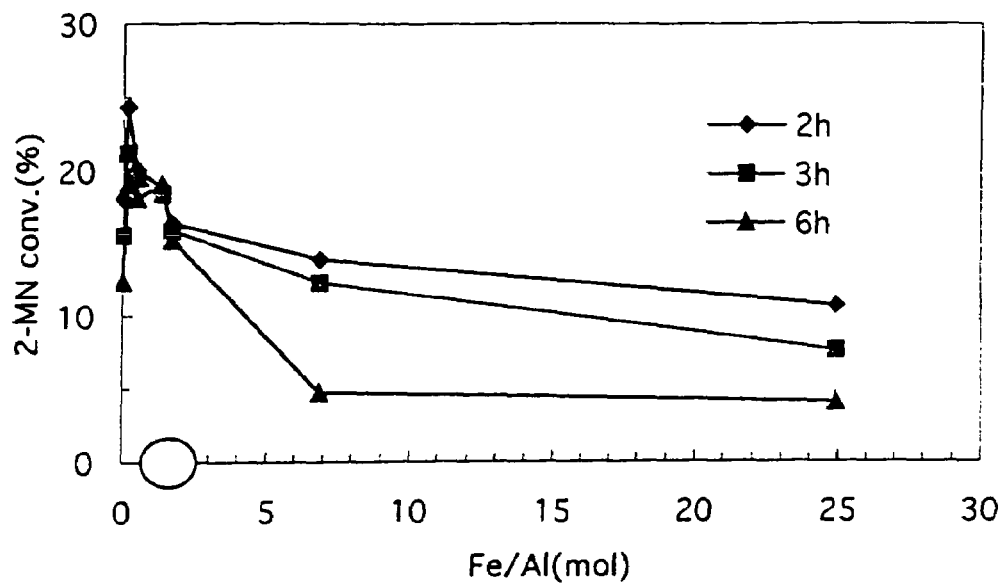
FIGS. 1a and 1b are graphs of the conversion of 2-MN under methylation conditions in accordance with our invention as a function of Fe/Al ratio at 2, 3 and 6 hours of catalyst run time.
Figure 1B:
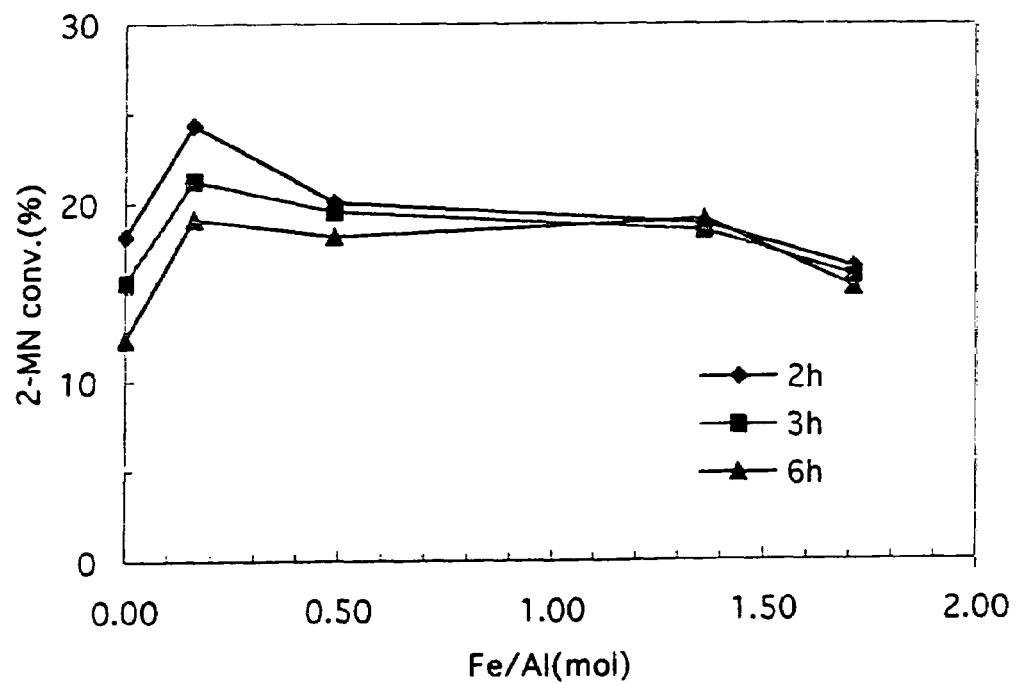
Figure 2A:
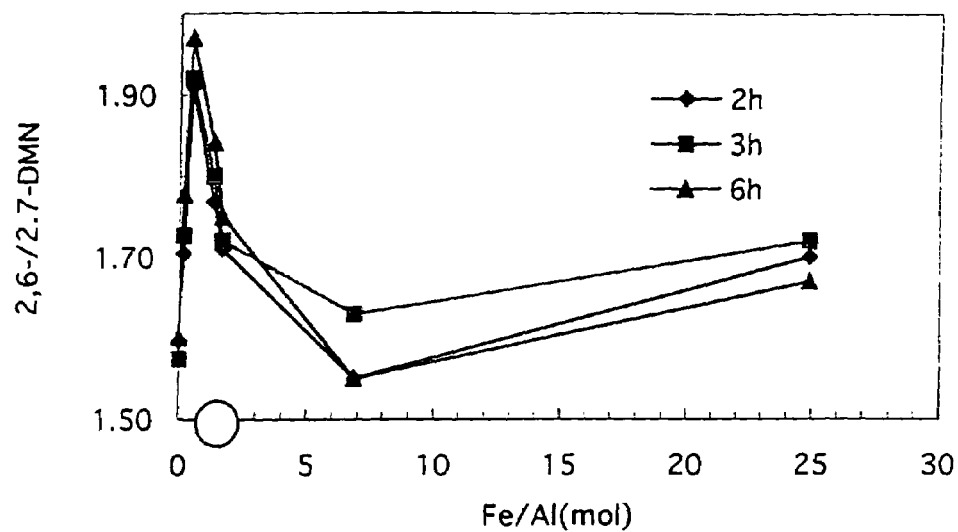
FIGS. 2a and 2b are graphs of the ratio of 2,6-DMN to 2,7-DMN obtained under methylation conditions in accordance with our invention as a function of Fe/Al ratio at 2, 3 and 6 hours of catalyst run time.
Figure 2B:
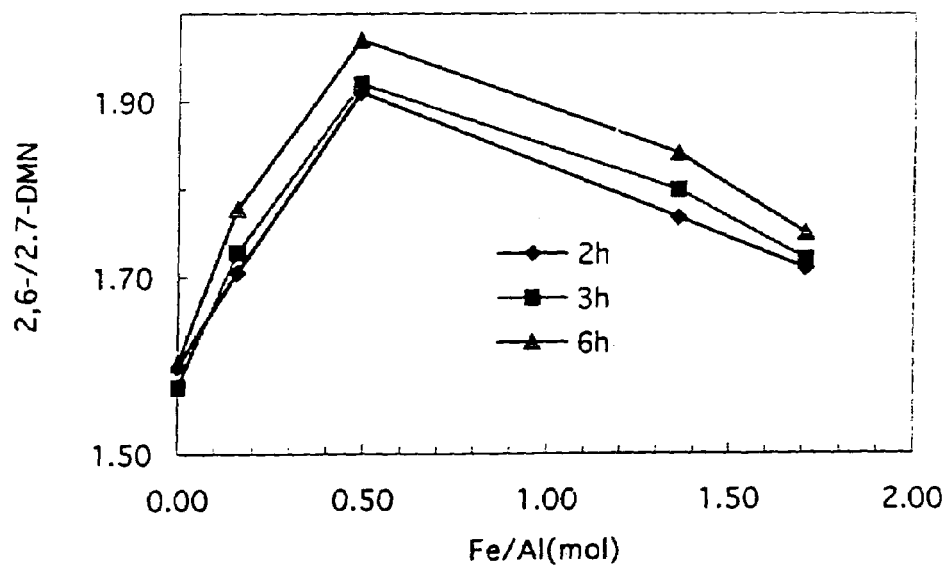
Figure 3A:
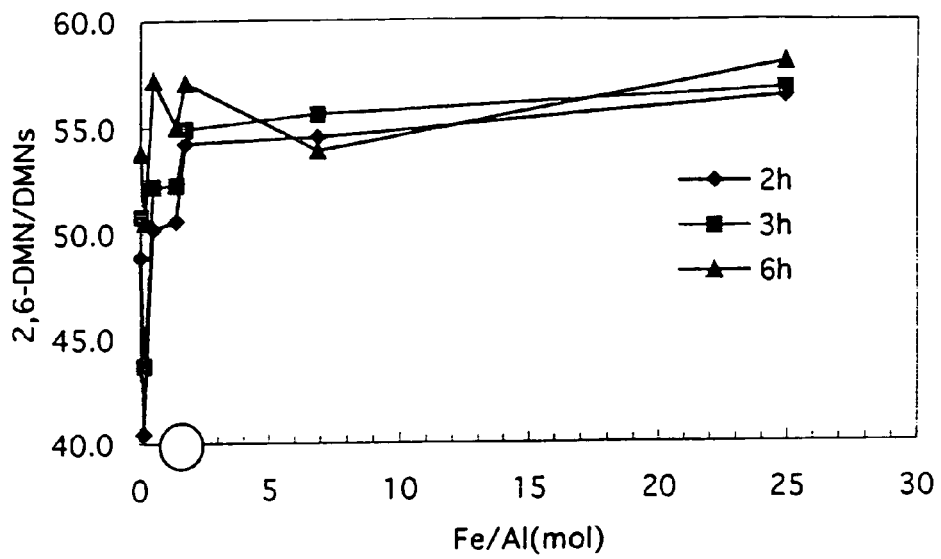
FIGS. 3a and 3b are graphs of the ratio of 2,6-DMN to all DMN's obtained under methylation conditions in accordance with our invention as a function of Fe/Al ratio at 2, 3 and 6 hours of catalyst run time.
Figure 3B:
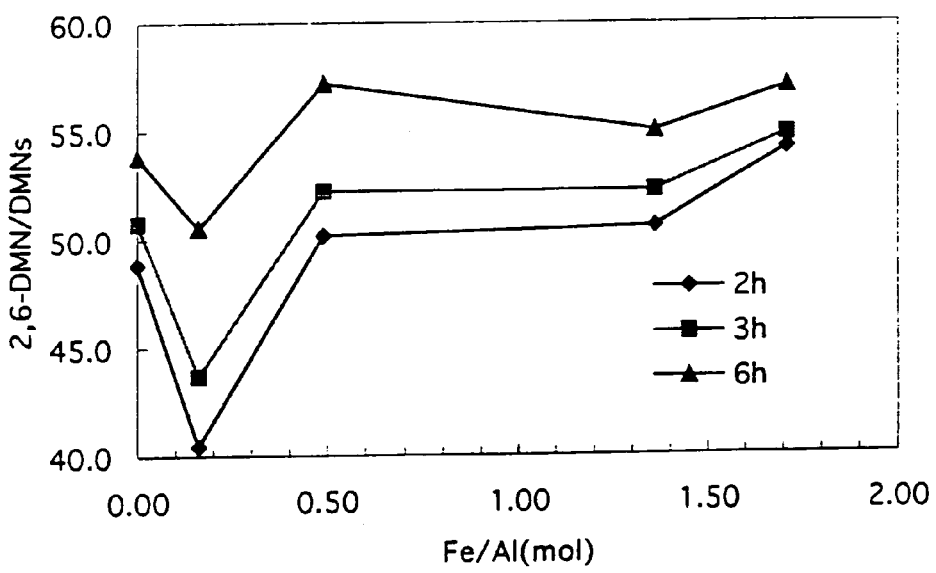
Figure 4A:
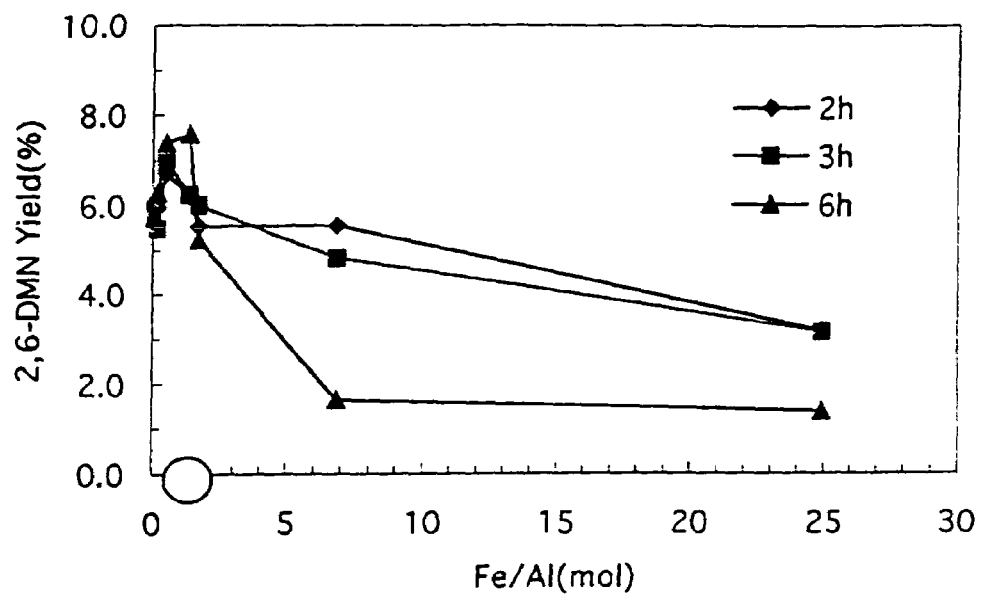
FIGS. 4a and 4b are graphs of the overall yield of 2,6-DMN obtained under methylation conditions in accordance with our invention as a function of Fe/Al ratio at 2, 3 and 6 hours of catalyst run time.
Figure 4B:
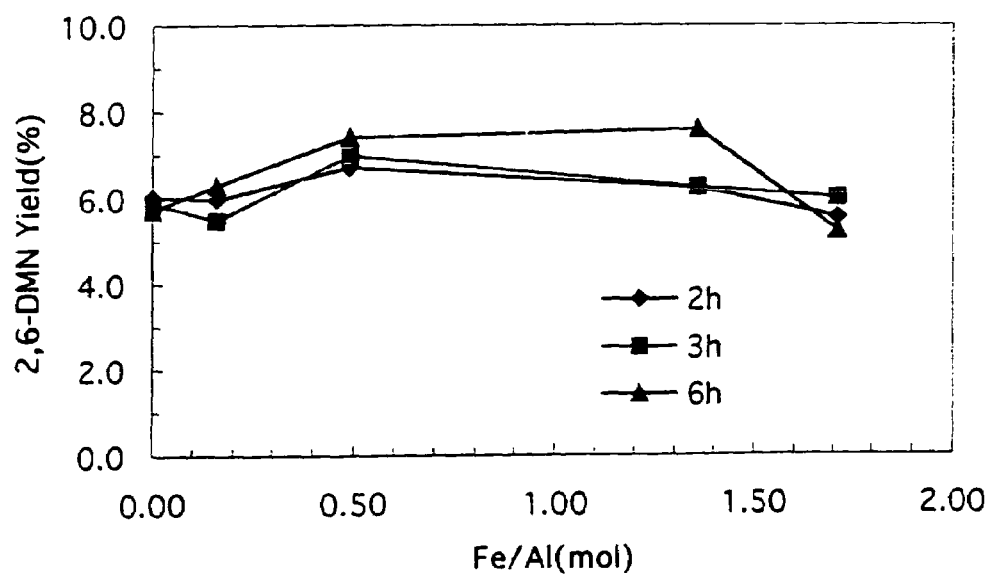

Described below are preferred embodiments of catalysts, catalyst preparation processes, and selective methylation processes in accordance with our invention. While the inventions are described in the context of the selective methylation of 2-MN to 2,6-DMN, those skilled in the art will recognize the applicability of our inventions to other methylation reactions, such as, for example, the conversion of 1-MN to 1,5-DMN, use of our novel catalysts in other aromatic alkylation reactions, and the preparation and use of other catalysts which incorporate a metal into a zeolitic lattice structure as described below.

Catalysts in accordance with our invention are characterized by the presence of one or more additional metals in addition to those typically found in an aluminosilicate zeolitic lattice structure. Unlike the Fe-MFI catalysts in which virtually all of the aluminum in the lattice has been replaced by iron, our catalysts contain significant amounts of both aluminum and one or more other metals, including Fe, Ga and/or Co. The catalysts can have a non-aluminum metal to aluminum ratio of between 1:10 to about 25:1, preferably to about 3:1. Preferably, the non-aluminum metal to aluminum ratio is between 1:8 and 3:1, and most preferably between 1:3 and 1.6:1.

The use of a single additional metal is preferred. As used in this application, the term "single additional metal" means that only a single metal is intentionally added to the zeolitic starting material. The use of the term "single additional metal" is not intended to preclude the presence of other trace metals which may be incorporated due to the presence of trace amounts of other metals present as impurities in reagents or feedstocks and which do not materially affect the performance of our catalysts.

Catalysts in accordance with our invention can be prepared in accordance with the isomorphic substitution process described in Example 1, below. As used in this application, "isomorphic substitution" means substitution of a portion of aluminum from a zeolitic starting material by another metal in a chemical process such as the one described below. We believe isomorphic substitution should result in at least 50 mole percent, preferably 75 mole percent, and most preferably up to about 100 mole percent of the added metal being incorporated directly in the zeolitic matrix. (see FIG. 5 and related discussion below).

EXAMPLE 1

A solution containing 0.086 grams of $FeF_3$ and 0.068 grams of $NH_4HF_2$ was dissolved in 100 milliliters of deionized water to provide a solution having a molar ratio of $FeF_3$ to $NH_4HF_2$ of 2:3. This solution was added with rapid agitation over one hour at a temperature of 92° C. to a 10 weight percent slurry in water of ZSM-5 type material known as CBV5020E available from the PQ Corporation of Valley Forge, Pa. The slurry contained 5 grams of the ZSM-5 material.

This mixture was refluxed for 24 hours, filtered, washed with deionized water, dried for 12 hours at 110° C., and calcined at a temperature of 450° C. for five hours. The resulting catalyst exhibiting a Fe/Al molar ratio of 0.49 was then pressed into pellets and sieved into a proper size (10–15 mesh) for use in the fixed bed reaction system.

Metal compounds useful for isomorphic substitution reactions preferably are soluble metal fluorides such as iron triflouride. Other useful soluble metal compounds will include those metal fluoride compounds such as $(NH_4)_2SiF_6$, $(NH4)_2TiF_6$, and $GaF_3 \cdot 3H_2O$.

The use of a soluble hydrogen fluoride salt agent such as $NH_4HF_2$ together with the soluble metal fluoride is preferred. The relative concentration of metal fluoride to soluble hydrogen salt is not critical and will vary with the number of metal atoms per mole of metal fluoride compound, the number and concentrations per mole of metal fluoride and soluble hydrogen fluoride salt, and the generic catalyst preparation conditions described below. In the case of $FeF_3$ and $NH_4HF_2$, a molar ratio of about 2:1 was found to be preferred.

Conditions effective for conducting an isomorphic substitution reaction will vary with the desired amount of substitution, but typically will include temperatures from about 0 to 350° C., and preferably from 60 to 100° C.; reflux times of from 0.5 to 72 hours, preferably from 4 to 24 hours; and soluble metal to zeolitic material metal (i.e. Al) ratios of from about 1:10 to 25:1, and preferably from 1:8 to 3:1.

The catalyst prepared in Example 1 was used to selectively methylate 2-MN to 2,6-DMN as described in Example 2, below.

EXAMPLE 2

A down-flow fixed bed reactor was loaded with 0.6 grams of catalyst comprising a mechanical mixture of 0.3 grams of the catalytic material prepared in Example 1 and 0.3 grams of a boehmite binder available as CAPTAPAL B ALUMINA from the Vista Chemical Company of Houston, Tex. The catalyst bed in the reactor was maintained at a temperature of 300° C. during the six-hour test period. Liquid feed containing methanol and 2-MN in a molar ratio of 5:1 was fed to the reactor at a rate of approximately 2 milliliters per hour, and an $N_2$ carrier gas was fed to the reactor at a rate of approximately 20 milliliters per minute. The reactor effluent was analyzed by gas chromatography and yielded the results in Table 1, below.

TABLE 1

| Measured Parameter | Result |
| --- | --- |
| 2-methylnaphthalene conversion | 20% |
| Selectivity to 2,6-DMN | 60% |
| 2,6-DMN to 2,7-DMN ratio | 2.2:1 |

As can be seen by comparing the results of Table 1 to the results reported for Fe-MFI catalysts described in the literature, the catalyst in accordance with our invention provides for improved 2-MN conversion, 2,6-DMN selectivity, and 2,6-DMN to 2,7-DMN ratio.

To determine the effect of iron to aluminum ratio in catalysts of the type described in Example 1, additional catalysts were prepared in accordance with Examples 3 to 8 below.

EXAMPLES 3–8

Catalyst was prepared as described in Example 1, except that the solution used to isomorphically substitute iron for aluminum in the ZSM-5 material was prepared by mixing the varying gram amounts of $FeF_3$ and $NH_4HF_2$ specified in Table 2 in 100 milliliters of deionized water. Each resulting catalyst exhibited the Fe/Al ratio listed in Table 2. Each catalyst was used to selectively methylate 2-MN as described in Example 2, except where noted to the contrary. The 2-MN conversion and selectivity to 2,6-DMN also are listed in Table 2. A graphical summary of 2-MN conversion, selectivity to 2,6-DMN, the ratio of 2,6-DMN to all DMN's, and the overall yield of 2,6-DMN for Examples 1 through 8 appear in FIGS. 1 through 4.

TABLE 2

| Example Number | $FeF_3$ (grams) | $NH_4HF_2$ (grams) | Fe/Al Ratio | 2-MN Conversion | 2,6-DMN Selectivity | 2,6/2,7 DMN Ratio |
| --- | --- | --- | --- | --- | --- | --- |
| 3 | 0.043 | 0.034 | 0.16 | 24.3 | 40.4 | 1.71 |
| 4 | 0.086 | 0.068 | 0.5 | 20.0 | 50.2 | 1.91 |
| 5 | 0.185 | 0.139 | 1.35 | 18.8 | 50.6 | 1.76 |
| 6 | 0.271 | 0.205 | 1.75 | 16.4 | 54.2 | 1.71 |
| 7 | 0.74 | 0.56 | 7.0 | 13.8 | 54.5 | 1.55 |
| 8 | 1.72 | 1.36 | 25 | 10.7 | 56.4 | 1.70 |

As can be seen by comparing the two-hour run time data in Table 2 and in the Figures, 2-MN conversion was highest in the range of 0.16:1 to 1.75:1 Fe/Al molar ratio, with maximum conversion occurring at around a Fe/Al molar ratio of 0.16:1.

The 2,6-DMN/2,7-DMN ratio peaked over the Fe/Al molar ratio range of 0.16:1 to about 7:1, with the 2,6-DMN/2,7-DMN ratio consistently above 1.7 at Fe/Al molar ratios in the range of 0.16:1 to 1.75:1.

2,6-DMN yields also peaked in the range of Fe/Al molar ratios from about 0.16:1 to 1.75:1.

These results demonstrate a marked superiority of catalysts in accordance with our invention when compared to prior art Fe-MFI catalysts used in naphthalenic methylation processes.

Metals most suitable for use in our invention include Fe, Ga, Co, and Ti and combinations thereof. The metals will be incorporated in the catalyst at metal to aluminum ratios of between about 0.1:1 to about 7:1, preferably about 0.1 to 2.9:1, and most preferably from about 0.16:1 to 1.75:1.

Other zeolites useful in preparing catalysts in accordance with our invention include ZSM-11, ZSM-12, ZSM-22, MCM-22, ZSM-23, ZSM-39, ZSM-57, mordenite, beta, FAU, and L-type zeolites. These zeolites are different from ZSM-5 in pore channel structure and in pore diameter, and are not believed to be as well suited to the methylation of 2-MN to 2,6-MN as a ZSM-5-type catalyst. However, we believe these other zeolites can be treated by our inventive process to prepare improved catalysts for other aromatic alkylation reactions.

While the use of a binder such as the boehmite binder used in Example 2 is preferred, the catalysts of the invention may be used without such a binder. When a binder is used, the weight ratio of binder to catalyst typically can range from 5 to 95, preferably from 20 to 80, and most preferably from 40 to 60. Although boehmite binders are preferred, other binders such as alkali earth metal oxides and $SiO_2$ may also be useful in practicing methylation reactions with our catalysts.

Catalysts in accordance with the present invention can be prepared by treating the aluminosilicates with different zeolite structures using the following general procedure: (1) prepare a solution using a given amount of metal fluoride (such as $FeF_3$, $CoF_3$, or $GaF_3$); (2) add a given amount of $NH_4HF_2$ to the solution of (1); (3) prepare a slurry of a zeolite in its proton form with a given structure (such as ZSM-5, ZSM-12, etc.) by adding a given amount of crystalline aluminosilicate into deionized water; (4) heat up the slurry to about 92° C. under reflux conditions; (5) add the solution prepared in step (2) to the slurry while the slurry is being mixed using a magnetic stirrer; (6) continue the reflux after the step (5) for 24 hours; (7) cool down the solid-liquid mixture and separate the solids by filtration; (8) dry the solid at 110° C. for about 12 hours; (9) calcine the dried solid at 450° C. for about 4 hours; (10) store the calcined sample in a desiccator for use as catalyst or for chemical analysis.

The amount of the metal incorporated in the catalyst is controlled by the type of non-aluminum metal compound; the ratio of halogen to metal compound; the ratio of solid to liquid in the reaction mixture; the speed of adding the metal compounds to the slurry of zeolites; the reaction temperature; and the duration of post-synthesis isomorphous substitution treatment.

Catalysts in accordance with the present invention are particularly useful for the reaction of naphthalenic feedstocks with methyl group donors under methylation conditions.

As used in this application, a "naphthalenic feedstock" means a compound having a naphthalenic ring system, either unsubstituted, i.e., naphthalene, or having one to three positions of the naphthalenic ring system substituted by one or more alkyl, carboxylic acid, alcohol, amine, alcohol or ester groups, such as monomethylnaphthalene (MN).

"Methyl group donor" means a compound capable of donating a methyl group to a naphthalenic feedstock under methylation conditions as described below, preferably methanol or dimethyl ether.

"Methylation conditions" means molar ratios of naphthalenic feedstock to methyl group donors in the range of 10:1 to 1:8, preferably between 7:1 to 1:5, at temperatures between about 25 and 600° C., preferably 200 and 450° C., and most preferably 275 and 375° C., pressures from between about 0 and 40 atmospheres, preferably 1 and 30, and most preferably 1 and 25 atmospheres, and weight hourly space velocities of about 0.1–30 $h^{-1}$, preferably 1.4 and 23 $h^{-1}$, and most preferably 2.9 and 11.5 $h^{-1}$.

While not wishing to be bound by any particular theory, we believe that the catalysts in accordance with the present invention are surprisingly effective because the iron and/or other metal added in the catalyst preparation process is substituted for aluminum in the zeolitic lattice. The incorporation of the iron into the lattice structure is suggested by temperature programmed hydrogen reduction spectra of the catalyst as performed in Example 9, below.

EXAMPLE 9

Catalyst from Example 4 was analyzed in the following manner by temperature programmed hydrogen reduction ("TPR") using a Micromeritics Autochem 2910 analyzer. 0.1 grams of catalyst was placed in the sample tube. A He carrier gas was passed through the sample tube until a gas chromatographic baseline was stable. At this point, the carrier gas was switched to 5.12 mole percent hydrogen in argon. The temperature of the sample was ramped up under computer control at a rate of 10° C. per minute from room temperature to 800° C.

Figure 5:
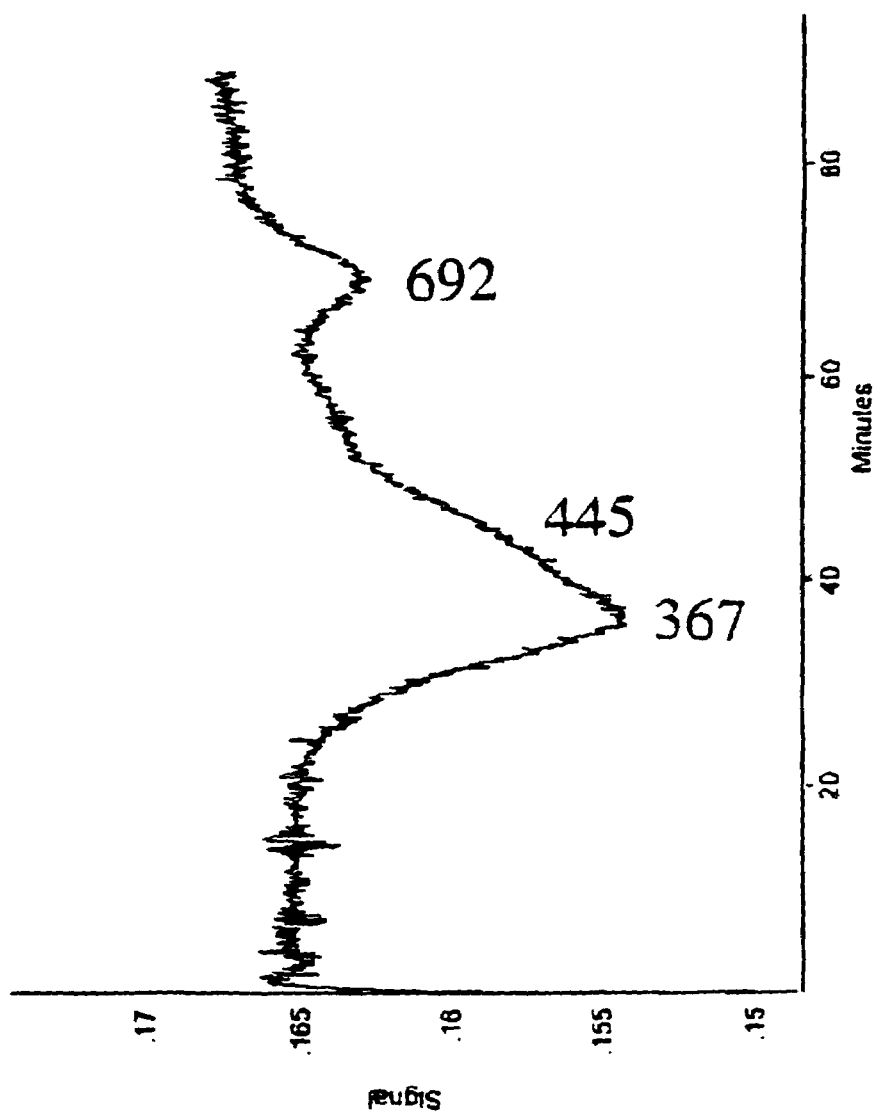
FIG. 5 is a temperature program reduction spectrum of a catalyst in accordance with the present invention.

The thermal conductivity ("TCD") signal was recorded by a computer data acquisition system. The TPR spectrum of Fe/ZSM-5 (Fe/Al=1/4) shows the reduction signal as a function of reduction temperature. There are at least two kinds of iron species in Fe/ZSM-5. The reduction peak at around 692° C. is believed to correspond to framework iron species, and the other two peaks at around 445° C. and 367° C. are related to ion-exchanged iron species and iron oxides such as $Fe_2O_3$ species, respectively. A representative temperature program reduction spectrum is shown in FIG. 5. The 692° C. peak corresponding to the iron framework species appears at about 70 minutes on the x-axis of FIG. 5.

Additional detail of the preferred embodiment of our catalysts can be gleaned from analysis of the x-ray diffraction (XRD) patterns of fluoride-treated catalyst. Compared to the XRD of the parent ZSM-5 sample before the treatment, the Fe/ZSM-5 catalysts prepared by the method in our invention show very similar XRD patterns including all the major peaks but at slightly different diffraction angles. This suggests that the crystal structure of the zeolitic material remained intact, and that Fe has been incorporated into the framework.

We have found that the performance of methylation catalysts in accordance with our invention can be further improved through the use of a binder having an added noble metal component as illustrated by Examples 10 and 11 below.

EXAMPLE 10

A catalyst according to the present invention having a Fe/Al ratio of 1:4 was prepared as in Example 1. The sample was then used to methylate 2-MN as described in Example 2. We found that the conversion of 2-MN decreased from its initial ~15% to ~10% after about 20 hours.

EXAMPLE 11

The experiment of Example 10 was repeated using a hybrid catalyst consisting of the 50 weight percent (0.3 grams) of the catalyst of Example 10 and 50 weight percent boehmite binder available as CAPTAPAL B ALUMINA from the Vista Chemical Company of Houston, Tex., to which had been added 0.4 weight percent platinum (based on total binder weight). The conversion of 2-MN remained at approximately 9 percent after 48 hours, demonstrating enhanced catalyst stability. Additionally, the DMN's produced included only 2,6-DMN, 2,7-DMN and 2,3-DMN.

The results of Examples 10 and 11 suggest that the stability of catalysts in accordance with the present invention can be enhanced by the use of noble metal additives such as platinum, palladium, rhodium, iridium, and ruthenium, preferably platinum and palladium, and most preferably platinum. The noble metal should be present between 0.01 and 5 weight percent, preferably between 0.05 and 2 weight percent, and most preferably about 0.1–0.4 weight percent. The noble metal can be added through the use of a metal-containing binder, as in Example 11, or added directly to the active component of the catalyst (i.e. the iron-containing ZSM-5 material) such as by the wet impregnation method, as is known in the art.

We have also found that some catalysts in accordance with our invention perform better if the catalysts are treated with $NH_4SiF_6$ either before or after addition of metal to the zeolytic material. It is believed that this treatment reduces the density of acid sites, thereby reducing coke formation at the lattice pore windows and on the catalyst surface and providing better access to the remaining acid sites located throughout the lattice. The results of one such experiment are illustrated in Example 12, below.

EXAMPLE 12

The experiment of Example 11 was repeated except that the catalyst was prepared by a two-step process. First, the zeolitic material was slurried and refluxed with $(NH_4)_2SiF_6$ by the same method used in Example 4. The catalyst was then prepared as in Example 4 using the treated zeolitic material. At 19 hours run time, the 2,6-DMN/2,7-DMN ratio increased from about 1.8:1 (EX. 11) to about 2:1, selectivity to 2,6-DMN (compared to all DMN's) increased from about 57% (EX. 11) to about 60% and activity remained at 8.2% (vs. 9.0 initial) even after about 70 hours. We believe from this experiment that in addition to the improved ratio and selectivity noted above, the stability of our catalyst is improved by treatment with $(NH_4)_2SiF_6$ before iron substitution, as evidenced by the good performance at 70 hours run time.

The reduction of catalyst acid sites can also be accomplished by other methods such as chemical vapor deposition (CVD) with Si compounds. Such Si compounds include $M_4OSi$ (where M is an alkyl or aromatic compound), or $SiH_4$. An alternative method for the positioning of acid sites on particle surface is the use of basic nitrogen compounds such as 2,4-dimethylquinoline, as described in Japanese patent document JP6329564, the disclosure of which is hereby incorporated by reference, or treatment with phosphorous-containing compounds as is known in the art.

Other embodiments of the invention will be apparent to those of ordinary skill in the art from our disclosure of our preferred embodiments and the additional teachings contained in this application. Our invention, therefore, is intended to be limited only by the scope of the following claims.

We claim:

1. A process for preparing an isomorphically substituted zeolitic catalyst comprising the steps of: selecting an aluminosilicate zeolitic material selected from the group consisting of ZSM-5, ZSM-11, ZSM-12, ZSM-22, MCM-22, ZSM-23, ZSM-39, ZSM-57, mordenite, Beta, FAU, and L-types; and refluxing, in the presence of $NH_4HF_2$, a slurry of the zeolitic material in the presence of a soluble metal compound selected from the group consisting of metal compounds of Fe, Ga, Ti, and Co and mixtures thereof under conditions effective for substituting aluminum in the aluminosilicate zeolitic material with metal from the soluble metal compound to yield a metal to aluminum ratio of between 1:10 and 3:1.

2. A process for preparing an isomorphically substituted zeolitic catalyst comprising the steps of: selecting ZSM-5 aluminosilicate zeolitic material and refluxing, in the presence of $NH_4HF_2$, a slurry of the zeolitic material in the presence of metal fluoride compounds under conditions effective for substituting aluminum in the aluminosilicate zeolitic material with metal from the soluble metal compound to yield a metal to aluminum ratio of between 1:10 and 3:1.

* * * * *